US008374692B2

(12) United States Patent
Bobgan et al.

(10) Patent No.: US 8,374,692 B2
(45) Date of Patent: Feb. 12, 2013

(54) IDENTIFYING A LEAD RELATED CONDITION BASED ON MOTION-BASED LEAD IMPEDANCE FLUCTUATIONS

(75) Inventors: Jean M. Bobgan, Maple Grove, MN (US); Timothy R. Brown, Maple Grove, MN (US); Patrick J. Garfield, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 282 days.

(21) Appl. No.: 12/828,127

(22) Filed: Jun. 30, 2010

(65) Prior Publication Data

US 2012/0004699 A1  Jan. 5, 2012

(51) Int. Cl.
*A61N 1/37* (2006.01)
(52) U.S. Cl. .......................................................... 607/28
(58) Field of Classification Search .............. 607/27–29
See application file for complete search history.

(56) References Cited

U.S. PATENT DOCUMENTS

| | | | |
|---|---|---|---|
| 5,117,824 A | 6/1992 | Keimel et al. | |
| 5,545,186 A | 8/1996 | Olson et al. | |
| 5,755,736 A | 5/1998 | Gillberg et al. | |
| 5,755,742 A | 5/1998 | Schuelke et al. | |
| 5,814,088 A | 9/1998 | Paul et al. | |
| 5,899,927 A * | 5/1999 | Ecker et al. | 607/23 |
| 6,760,624 B2 | 7/2004 | Anderson et al. | |
| 7,266,409 B2 | 9/2007 | Gunderson | |
| 7,289,851 B2 | 10/2007 | Gunderson et al. | |
| 2005/0154421 A1 | 7/2005 | Ousdigian | |
| 2006/0224222 A1 | 10/2006 | Bradley et al. | |
| 2007/0270914 A1 | 11/2007 | Vincent et al. | |
| 2008/0161870 A1 | 7/2008 | Gunderson | |
| 2008/0172098 A1 | 7/2008 | Gunderson | |
| 2008/0215110 A1 | 9/2008 | Gunderson | |
| 2009/0112292 A1 * | 4/2009 | Armstrong | 607/63 |
| 2009/0299421 A1 | 12/2009 | Sawchuk et al. | |
| 2010/0114204 A1 | 5/2010 | Burnes et al. | |

FOREIGN PATENT DOCUMENTS

| | | | |
|---|---|---|---|
| WO | 9842406 A1 | 10/1998 | |
| WO | 2009054908 A1 | 4/2009 | |

OTHER PUBLICATIONS

International Search Report and Written Opinion of international application No. PCT/US2011/1033993, dated Nov. 3, 2011, 12 pp.
Reply to Written Opinion from corresponding PCT application serial No. PCT/US2011/033993 filed Apr. 27, 2012, (9 pages).
International Preliminary Report on Patentability from corresponding PCT application serial No. PCT/US2011/033993 dated Jul. 3, 2012 (12 pages).

* cited by examiner

*Primary Examiner* — Brian T Gedeon
(74) *Attorney, Agent, or Firm* — Stephen W. Bauer; Michael J. Ostrom

(57) ABSTRACT

Techniques for determining whether a lead related condition exists based on a correlation between a parameter indicative of impedance of a lead and a parameter indicative of motion of the lead. In some examples, the techniques include generating an electrical signal that is indicative of impedance of the lead, generating an electrical signal that is indicative of motion of the lead, and monitoring the frequency, amplitude, and phase of the electrical signals in order to identify a correlation. In some examples, if a lead related condition is identified, an alert is provided or a sensing or therapy modification is suggested.

17 Claims, 10 Drawing Sheets

IDENTIFYING A LEAD RELATED CONDITION BASED ON MOTION-BASED LEAD IMPEDANCE FLUCTUATIONS

TECHNICAL FIELD

The invention relates to medical devices, and, more particularly, to collection and analysis of diagnostic information by medical devices.

BACKGROUND

A variety of implantable medical devices for delivering a therapy and/or monitoring a physiological condition have been clinically implanted or proposed for clinical implantation in patients. Some implantable medical devices deliver electrical stimulation to, and/or monitor conditions associated with, the heart, muscle, nerve, brain, stomach or other organs or tissue. Some implantable medical devices employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead, which may be implanted at the desired location. A proximal portion of the lead may be coupled to an implantable medical device housing, which may contain circuitry such as signal generation and/or sensing circuitry.

Some implantable medical devices, such as cardiac pacemakers or cardioverter-defibrillators, provide therapeutic electrical stimulation to the heart via electrodes carried by one or more implantable leads. The electrical stimulation may include signals such as pulses or shocks for pacing, cardioversion, or defibrillation. In some cases, an implantable medical device senses intrinsic depolarizations of the heart, and controls delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Implantable medical leads associated with an implantable medical device typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within the connected implantable medical device housing to respective electrodes or sensors. Some electrodes may be used for both stimulation and sensing. Each electrical conductor is typically electrically isolated from other electrical conductors, and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in leads or connections may result in intermittent or continuous short circuits, open circuits, or changes in lead impedance.

Short circuits, open circuits, or significant changes in impedance may be referred to, in general, as lead related conditions. In the case of cardiac leads, sensing of an intrinsic heart rhythm through a lead can be altered by lead related conditions. Structural modifications to leads, conductors, or electrodes may alter sensing integrity. Furthermore, impedance changes in the stimulation path due to lead related conditions may affect sensing and stimulation integrity for pacing, cardioversion, or defibrillation.

In many cases, an implantable medical device system monitors the impedance of the one or more conductors in an implantable medical lead to detect whether a lead related condition, e.g., a fracture of one or more of the conductors, has occurred. Typically, an implantable medical device periodically, e.g., on the order of once per day, measures impedances of a plurality of electrical paths that each include one or more of the conductors. In some examples, lead related conditions can be detected by measuring the impedance of an electrical path between two or more electrodes on one or more leads, the electrical path including one or more conductors within the one or more leads. Changes in impedance of an electrical path can be indicative of a fractured conductor, or insulation failure, as examples.

The implantable medical device or another component of an implantable medical device system compares the measured impedance to one or more thresholds. A threshold may be a predetermined threshold, e.g., based on a specification of a lead or a baseline impedance measurement taken at or shortly after implant of the lead, or may be an adaptive threshold determined based on a number of previous impedance measurements, e.g., a mean or median of the N most recent impedance measurements. In either case, the implantable medical device system may identify a lead related condition if, for example, the measured impedance exceeds a threshold, and may take some action based on the identification, e.g., provide an alert to the patient or a clinician.

SUMMARY

Certain types of conductor fractures may not be readily detectable by the above-described impedance monitoring technique. For example, if the electrical conductors have fractured, but are still in intimate contact with each other, the impedance of the lead at the time of a measurement may not exceed a threshold. As another example, conductors of an implantable medical lead may comprise a plurality of conductive, threadlike strands that collectively form a conductor cable, and some of the strands of a particular conductor cable may be fractured while other strands remain intact, e.g., the conductor cable is not entirely fractured. However, in such cases, impedance fluctuations that are relatively small when compared to the threshold may be evident.

In general, the disclosure is directed to techniques for determining whether a lead related condition exists based on a correlation between a parameter indicative of impedance of the lead and a parameter indicative of motion of the lead. In situations in which portions of a fractured electrical conductor are still intact or in intimate contact with each other, motion of a lead may result in fluctuations in the impedance of an electrical path including the fractured conductor due to changes in the amount of conductor in electrical contact as a result of the movement. Detection of a lead related condition based on identification of a correlation between impedance and motion of a lead may allow earlier detection of lead fracture, e.g., while the portions of the fractured lead are still intact or in intimate contact. However, in some examples, it may be desirable to identify conductors in which several of the strands are fractured, even if the remaining strands are intact. For example, sensing or stimulation capabilities of a particular conductor may be less effective in examples in which several of the strands of the conductor are fractured. Furthermore, the partial fracture may eventually develop into a complete fracture, which may further impact the sensing or stimulation capabilities of the conductor.

In one example, a method comprises monitoring a parameter indicative of impedance of a lead, monitoring a parameter indicative of motion of the lead, identifying a correlation between the parameter indicative of impedance of a lead and the parameter indicative of motion of the lead, and identifying a lead related condition based on the correlation.

In another example, a system comprises a processor that monitors a parameter indicative of impedance of a lead, monitors a parameter indicative of motion of the lead, identifies a correlation between the parameter indicative of impedance of a lead and the parameter indicative of motion of the lead, and identifies a lead related condition based on the correlation.

In another example, a system comprises means for monitoring a parameter indicative of impedance of a lead, means for monitoring a parameter indicative of motion of the lead, means for identifying a correlation between the parameter indicative of impedance of a lead and the parameter indicative of motion of the lead, and means for identifying a lead related condition based on the correlation.

In another example, a computer-readable storage medium comprises instructions that cause a processor to monitor a parameter indicative of impedance of a lead, monitor a parameter indicative of motion of the lead, identify a correlation between the parameter indicative of impedance of a lead and the parameter indicative of motion of the lead, and identify a lead related condition based on the correlation The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
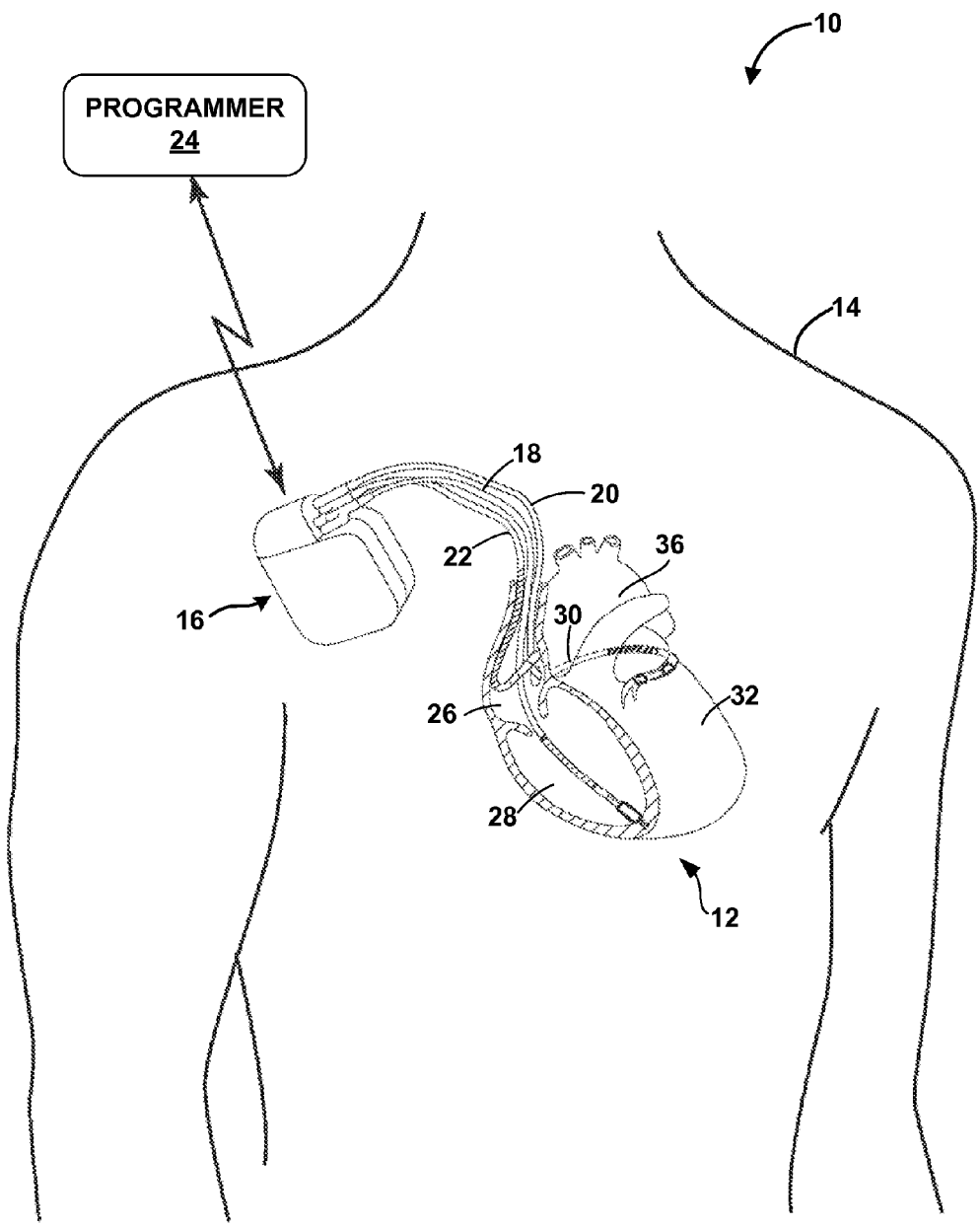
FIG. 1 is a conceptual diagram illustrating an example system comprising an implantable medical device (IMD) for sensing the electrical activity of a heart of a patient and/or delivering electrical stimulation therapy to the heart via implantable leads.

FIG. 1 is a conceptual diagram illustrating an example system 10 that monitors and/or provides therapy to a heart 12 of a patient 14. System 10 includes implantable medical device (IMD) 16, which is coupled to implantable leads 18, 20 and 22. Thus, system 10 may be referred to as an implantable medical device system. IMD 16 may be, for example, an implantable pacemaker, cardioverter, and/or defibrillator that senses electrical activity within heart 16 and provides electrical signals to heart 12 via electrodes coupled to leads 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12. In some alternative embodiments, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. In some examples, IMD 16 provides pacing pulses as part of a cardiac resynchronization therapy (CRT) or anti-tachycardia pacing therapy (ATP).

IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver ATP, or cardioversion or defibrillation therapy, to heart 12 in the form of electrical pulses. In some examples, IMD 16 may be programmed to deliver a progression of therapies, e.g., ATP followed by defibrillation, or pulses with increasing energy levels, until a tachyarrhythmia of heart 12 is stopped. IMD 16 detects tachycardia or fibrillation employing one or more tachycardia or fibrillation detection techniques known in the art.

In the example of FIG. 1, system 10 also includes a programmer 24. In some examples, programmer 24 may be a handheld computing device, computer workstation, or networked computing device. A user, such as a physician, technician, surgeon, electrophysiologist, or other clinician, may interact with programmer 24 to communicate with IMD 16.

For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16.

The user may use programmer 24 to program a therapy progression, select electrodes used to deliver defibrillation pulses, select waveforms for the defibrillation pulses, or select or configure a fibrillation detection algorithm for IMD 16. The user may also use programmer 24 to program similar aspects of other therapies provided by IMD 16, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 is an example of a device that monitors a parameter indicative of impedance of a lead, e.g., leads 18, 20, or 22, and a parameter indicative of motion of the lead, and determines that a lead related condition exists based on identifying a correlation between the parameters. As used herein, an impedance of a lead or a lead impedance may refer to an impedance of an electrical path that includes one or more conductors of the lead.

In some examples, sensing circuitry coupled to particular electrodes of leads 18, 20, or 22 may receive signals that are indicative of impedance of the leads and signals that are indicative of motion of the leads within IMD 16. In some examples, a sensor of system 10 other than electrodes of leads 18, 20, or 22 may provide a signal indicative of motion of leads 18, 20, or 22. IMD 16 may analyze the signals to determine whether a correlation exists between particular parameters of the signals. For example, IMD 16 may determine whether a correlation exists between a characteristic of the signal indicative of impedance of a lead and a characteristic of the signal indicative of motion of the lead. If IMD 16 identifies a correlation, IMD 16 may determine that a lead related condition exists. In some examples, IMD 16 may automatically perform a therapy or sensing modification if IMD 16 determines that a lead related condition exists. Additionally or alternatively, programmer 24 may receive and display an alert or a suggestion for therapy or sensing modifications to a user if IMD 16 determines that a lead related condition exists.

In other examples, one or more devices other than IMD 16 may, alone or in combination with IMD 16, implement the techniques described herein. For example, programmer 24 or another external device may store signals or data received from IMD 16, such as signals or data that are indicative of impedance of the leads and signals or data that are indicative of motion of the leads. Programmer 24 or another external device may monitor a particular parameter of the signals or data in order to determine whether a correlation exists. If programmer 24 or another external device identifies a correlation, programmer 24 or another external device may determine that a lead related condition exists. Subsequently, programmer 24 or another external device may display an alert or suggestion for therapy or sensing modification to a user, or may automatically modify the therapy or sensing provided by IMD 16.

Furthermore, although described in the context of an implantable medical device system including an implantable cardiac device, the techniques described herein may be applicable to other implantable medical device systems including other implantable medical devices that may be coupled to one or more leads. For example, the techniques described herein may be applicable to implantable medical device systems comprising other implantable medical devices that deliver therapeutic stimulation via one or more leads, such as spinal cord stimulators, deep brain stimulators, or other implantable neurostimulators. Furthermore, in some examples, the medical device and/or leads are not implanted.

Figure 2:
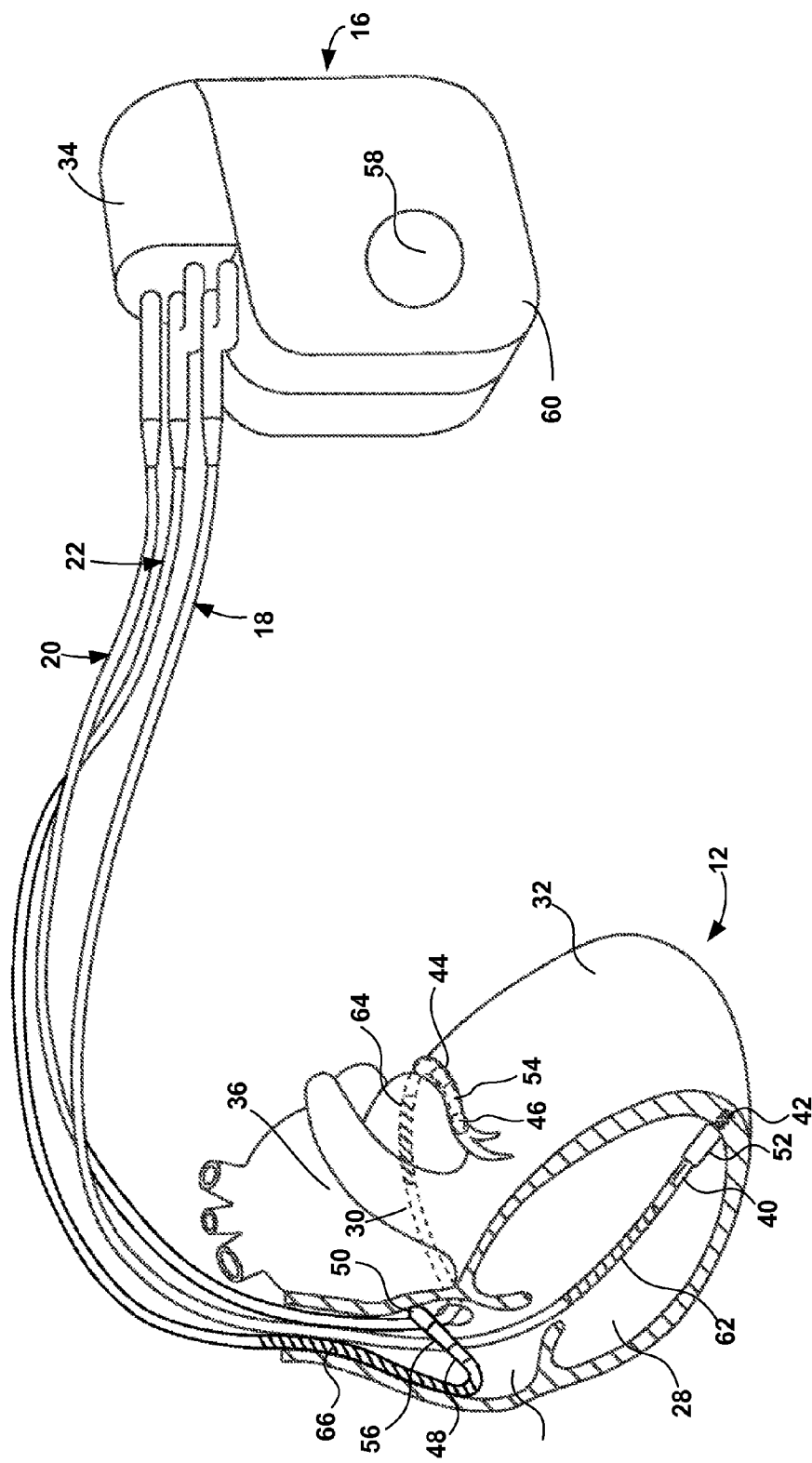
FIG. 2 is a conceptual diagram further illustrating the IMD and leads of the system of FIG. 1 in conjunction with the heart.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36 in the illustrated example, but other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some embodiments may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode may be configured as appropriate for the application of the sensing electrode configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3.

Figure 3:
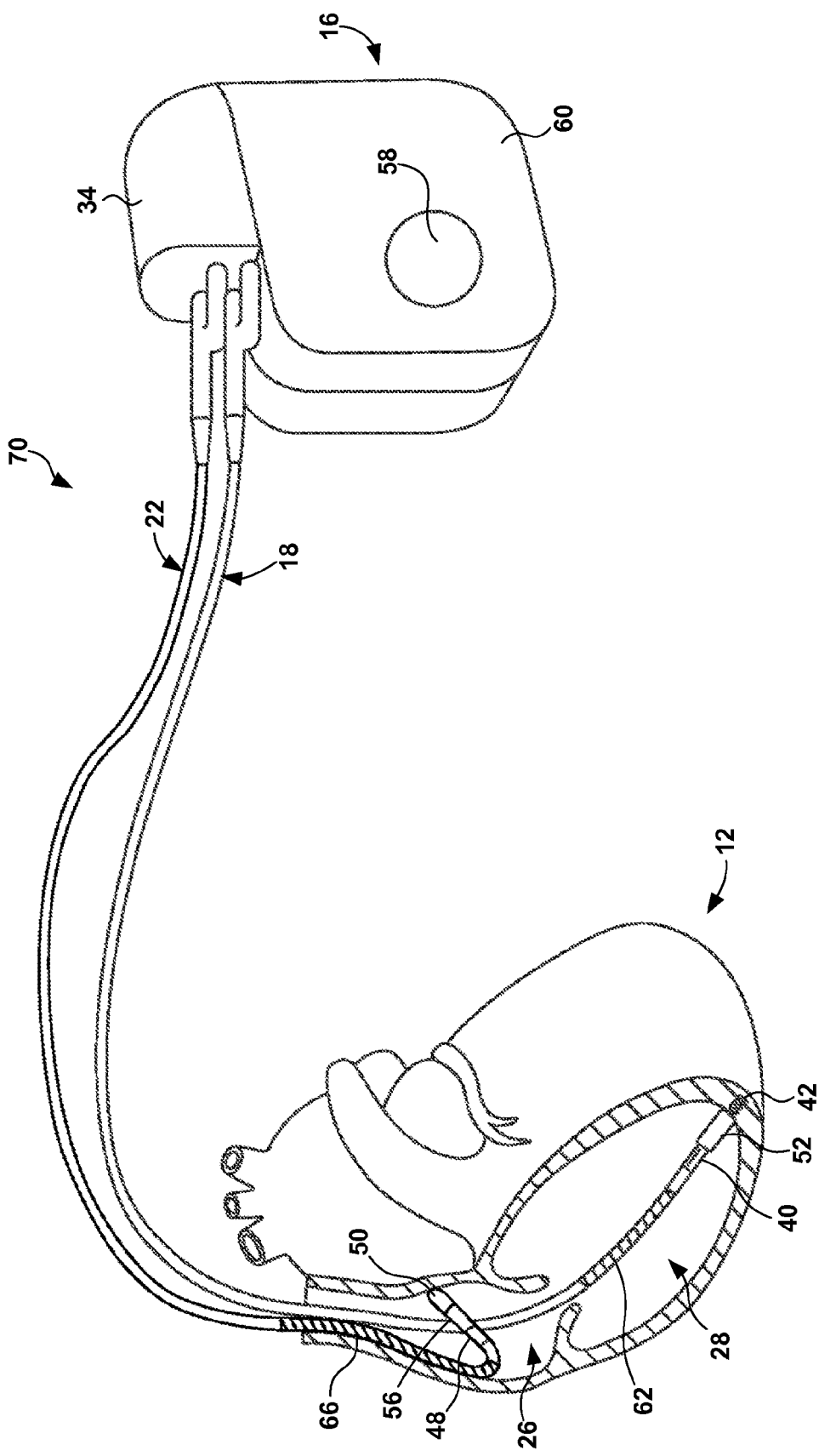
FIG. 3 is a conceptual diagram illustrating another example therapy system comprising the IMD of FIG. 1 coupled to a different configuration of leads.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Identifying a lead related condition according to the techniques described herein may also be performed by or with respect to system 70.

Figure 4A:
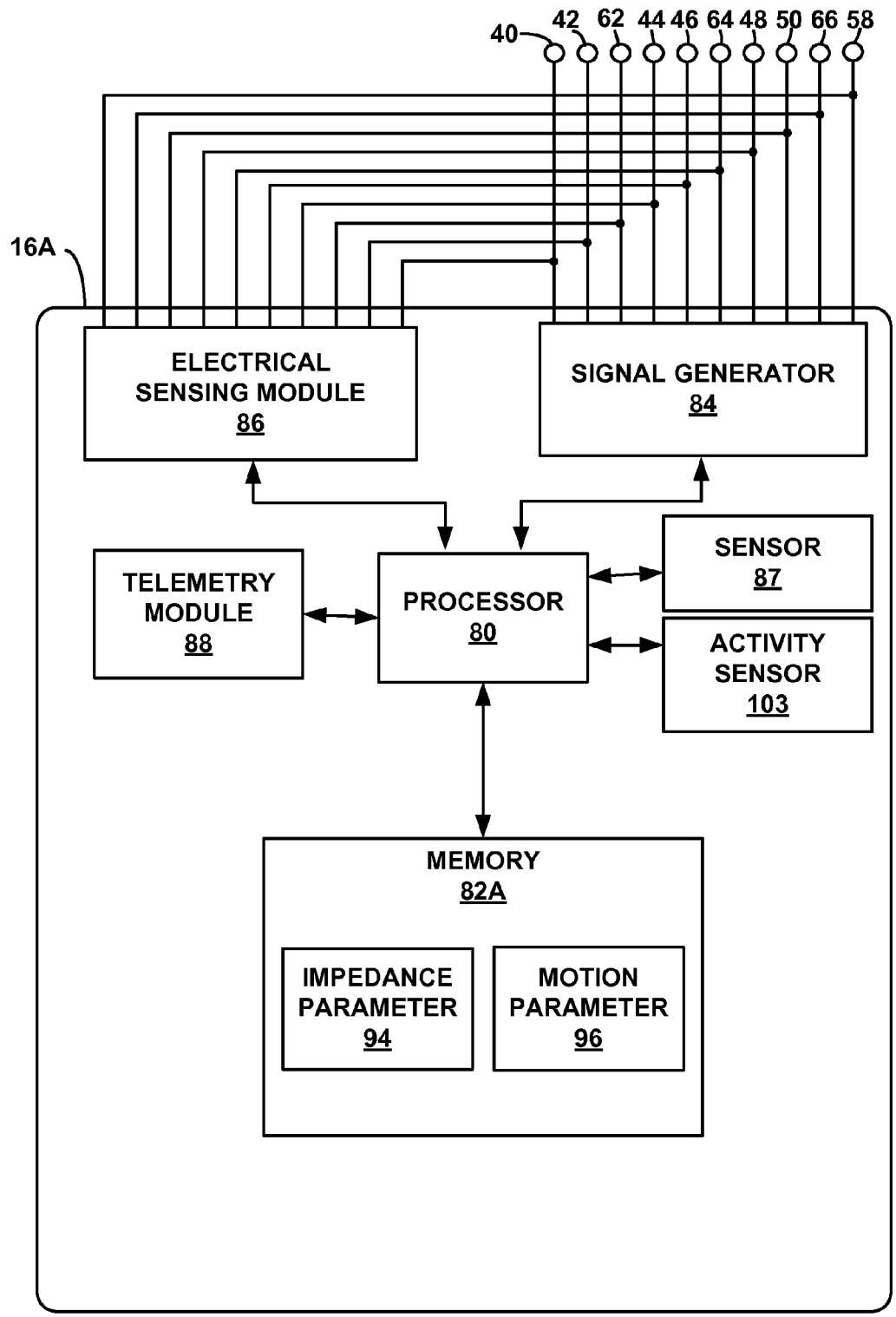
FIGS. 4A and 4B are functional block diagrams illustrating example configurations of the IMD of FIG. 1.

FIG. 4A is a functional block diagram illustrating an example configuration of IMD 16A. In the example illustrated by FIG. 4A, IMD 16A includes a processor 80, memory 82A, signal generator 84, electrical sensing module 86, sensor 87, telemetry module 88 and activity sensor 103. Memory 82A may include computer-readable instructions that, when executed by processor 80, cause IMD 16A and processor 80 to perform various functions attributed to IMD 16A and processor 80 herein. Memory 82A may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls signal generator 84 to deliver stimulation therapy to heart 12. Processor 80 may control signal generator 84 to deliver stimulation according to selected algorithms and parameter values, which may be stored in memory 82A.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16A. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver pacing, cardioversion, or defibrillation pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing electrode configuration, via the switch module within electrical sensing module 86, e.g., by providing signals via a data/address bus. Electrical sensing module 86 may include multiple detection channels, each of which may comprise an amplifier. In response to the signals from processor 80, the switch module of electrical sensing module 86 may couple selected electrodes to each of the detection channels.

Processor 80 may include a timing and control module, which may be embodied as hardware, firmware, software, or any combination thereof. The timing and control module may comprise a dedicated hardware circuit, such as an ASIC, separate from other components of processor 80, such as a microprocessor, or a software module executed by a component of processor 80, which may be a microprocessor or ASIC. If IMD 16A is configured to generate and deliver pacing pulses to heart 12, the timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may define a blanking period, and provide signals to electrical sensing module 86 to blank one or more channels, e.g., amplifiers, for a period during and after delivery of electrical stimulation to heart 12. The durations of these intervals may be determined by processor 80 in response to stored data in memory 82A. The timing and control module of processor 80 may also determine the amplitude of the cardiac pacing pulses.

During pacing, escape interval counters within the timing and control module of processor 80 may be reset upon sensing of R-waves and P-waves with detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by signal generator 84, and thereby control the basic timing of cardiac pacing functions, including anti-tachyarrhythmia pacing.

In some examples, a portion of memory 82A may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia. In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NONLETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian are incorporated herein by reference in their entireties. However, other arrhythmia detection methodologies may also be employed by processor 80 in other examples.

In some examples, processor 80 stores data related to a parameter indicative of impedance of a lead as impedance parameter data 94 in memory 82A and data related to a parameter indicative of motion of the lead as motion parameter data 96 in memory 82A. For example, in some examples, processor 80 may receive signal data from electrical sensing module 86, sensor 87, activity sensor 103, or another component of IMD 16A and store the signal data as impedance parameter data 94 or motion parameter data 96. In some examples, electrical sensing module 86 generates a signal indicative of impedance of the lead, and processor 80 can store data representing or derived from the signal as impedance parameter data 94. Similarly, electrical sensing module 86, sensor 87, and/or activity sensor 103 may generate a signal indicative of motion of the lead, and processor 80 can store data representing or derived from the signal as motion parameter data 96.

In the event that processor 80 detects an atrial or ventricular tachyarrhythmia based on signals from electrical sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16A is configured to generate and deliver cardioversion or defibrillation shocks to heart 12, signal generator 84 may include a high voltage charge circuit and a high voltage output circuit. In the event that generation of a cardioversion or defibrillation shock is required, processor 80 may employ the escape interval counter to control timing of such cardioversion and defibrillation shocks, as well as associated refractory periods.

IMD 16A may comprise one or more sensors, such as sensor 87 and activity sensor 103 illustrated in the example of FIG. 4A. Sensors 87 and 103 may be within housing 60 (FIG. 2) of IMD 16A. IMD 16A may additionally or alternatively be coupled to one or more sensors located outside of housing 60 of IMD 16A. For example, sensors 87 and 103 may be located on or within one or more of leads 18, 20 and 22, or another lead which may or may not include stimulation/sensing electrodes. In some examples, sensors 87 and 103 may be separately housed from IMD 16A, and may be coupled to IMD 16A via wireless communication. Sensor 87 and 103 may be implanted or external.

In some examples, sensor 87 may comprise any sensor capable of generating a signal representative of mechanical activity, e.g., contraction, of heart 12. For example, sensor 87 may comprise a pressure sensor, a motion sensor, or a heart sound sensor. A pressure sensor may be, for example, a capacitive pressure sensor that senses an intracardiac or other cardiovascular pressure. A motion sensor may be, for example, an accelerometer or piezoelectric element. A heart sound sensor may comprise, for example, an accelerometer or a microphone. Processor 80 may receive one or more signals from sensor 87 or a plurality of sensors. Processor 80 may monitor, among other things, the mechanical activity of heart 12 based on such signals.

Activity sensor 103 may comprise any sensor that provides a signal as a function of activity of patient 14, e.g., motion of patient 14 or any portion of the patient, such as footfalls. Activity sensor 103 may comprise, as examples, one or more accelerometers, piezoelectric elements, mercury switches, gyroscopes, or the like. In some examples, activity sensor 103 may comprises a plurality of substantially orthogonally aligned accelerometers, e.g., a multi-axis accelerometer, and may provide a signal indicative of posture of patient 14.

Figure 4B:
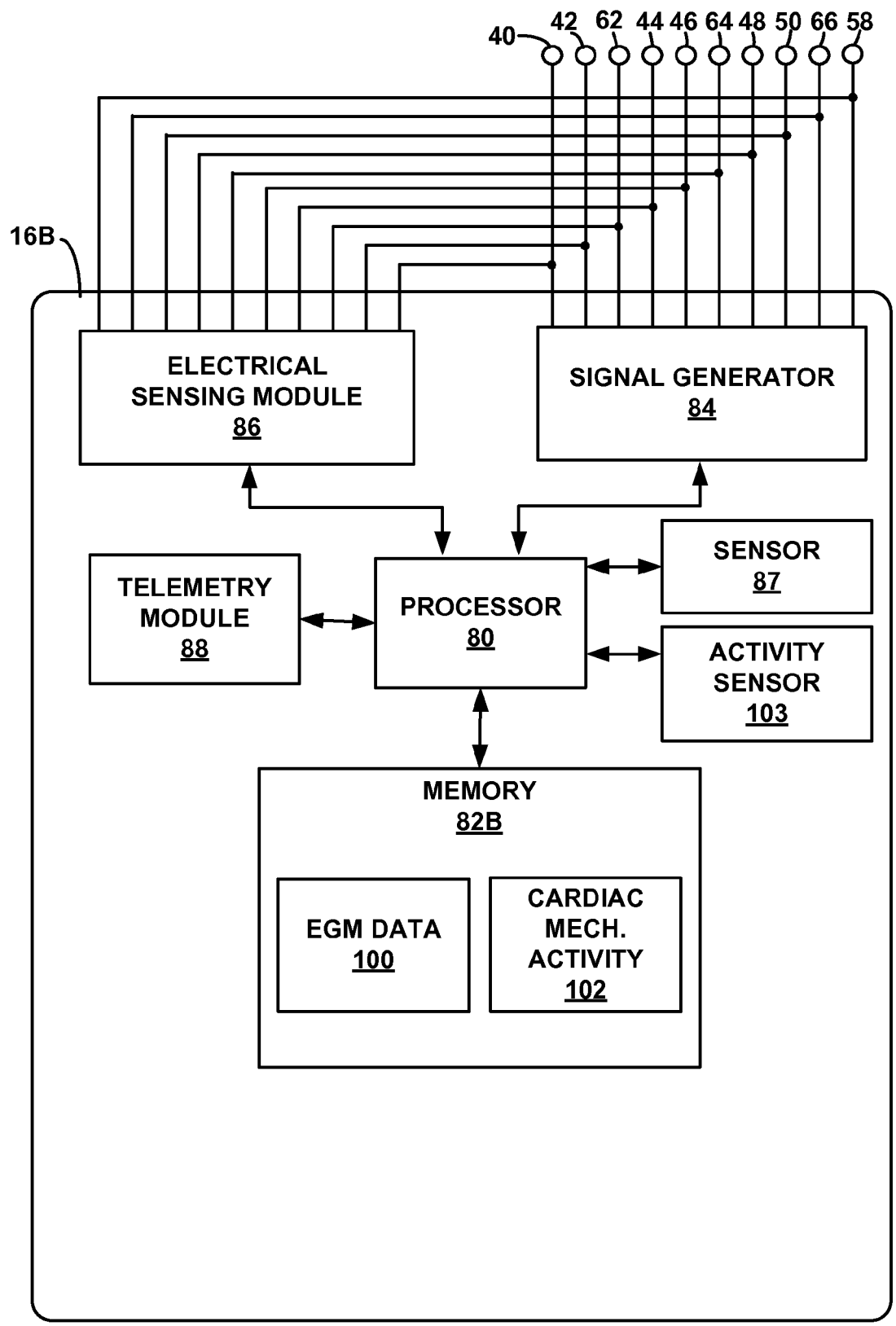

FIG. 4B is a functional block diagram illustrating another example configuration of IMD 16B. In the example illustrated by FIG. 4B, IMD 16B also includes a processor 80, memory 82B, signal generator 84, electrical sensing module 86, sensor 87, telemetry module 88, and activity sensor 103. The components of IMD 16B function substantially similarly to the like named and numbered components of IMD 16A of FIG. 4A.

As discussed with respect to FIG. 4A, processor 80 can store data related to a parameter indicative of impedance of a lead and data related to a parameter indicative of motion of the lead in memory 82B. In the example illustrated in FIG. 4B, memory 82B includes EGM data module 100 and cardiac mechanical activity module 102.

Figure 5:
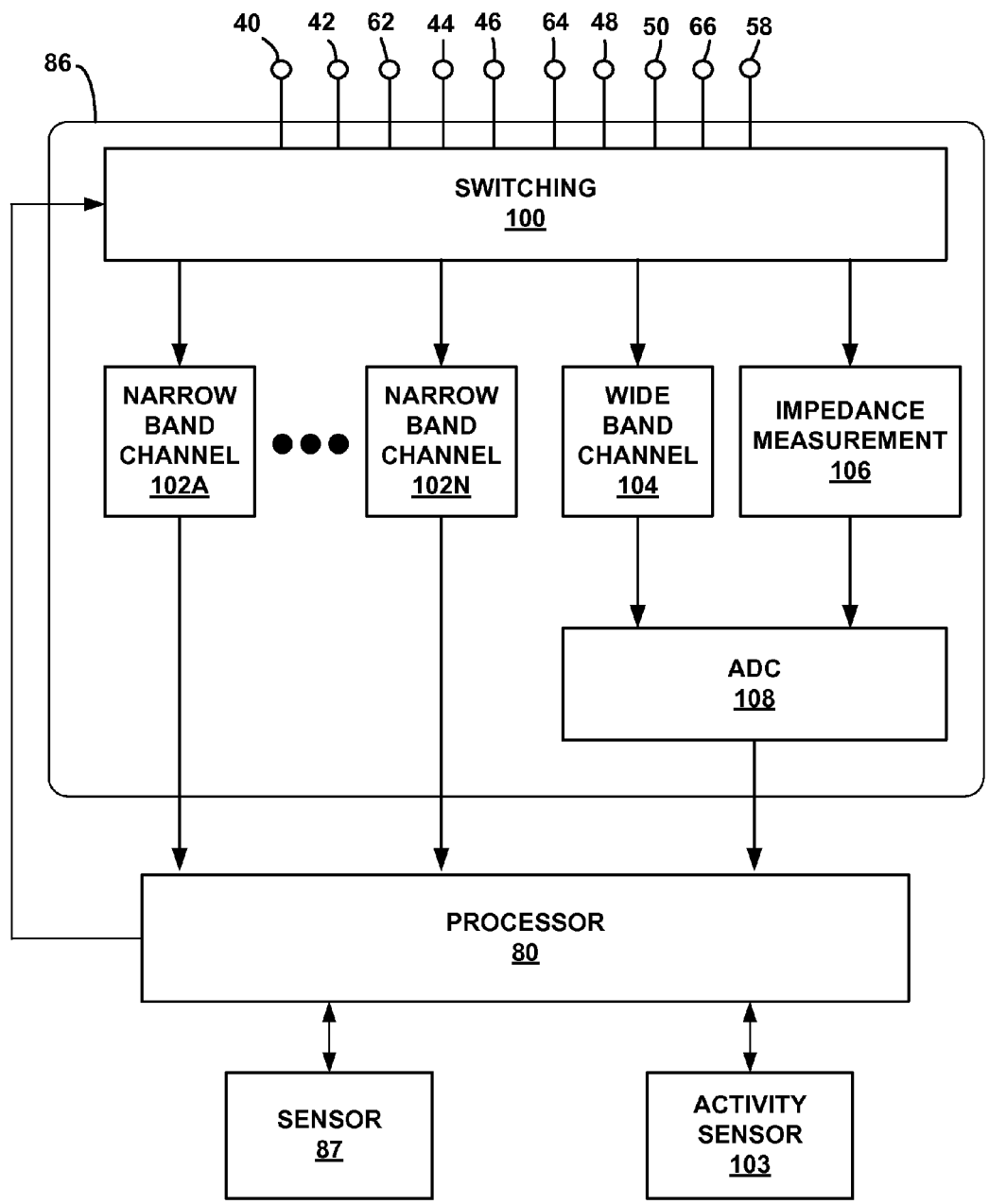
FIG. 5 is a functional block diagram illustrating an example electrical sensing module of the IMD of FIG. 1.

In some examples, as discussed in further detail with respect to FIG. 5, fluctuations in an EGM signal can be indicative of impedance of a lead. Memory 82B of IMD 16B includes EGM data 100, and processor 80 can store EGM data sensed by electrical sensing module 86 as EGM data 100. Processor 80 can access the data stored as EGM data 100 in order to monitor a parameter indicative of impedance of a lead.

As also discussed in further detail with respect to FIG. 5, mechanical activity of heart 12 can correspond to motion of the lead, particularly in examples in which the lead is implanted proximate to or within, e.g., attached to, heart 12. That is, motion of heart 12 can result in motion of the lead if the lead is implanted proximate to or within heart 12. Consequently, data indicative of mechanical activity of heart 12 may also be representative of motion of the lead. In some examples, processor 80 stores data indicative of mechanical activity of heart 12 as cardiac mechanical activity data 102 and accesses the data in order to monitor a parameter indicative of motion of the lead.

FIG. 5 is a block diagram of an example configuration of electrical sensing module 86, sensor 87, activity sensor 103, and processor 80 (FIGS. 4A and 4B). As shown in FIG. 5, electrical sensing module 86 includes multiple components including a switching module 100, narrow band channels 102A to 102N (collectively "narrow band channels 102"), wide band channel 104, impedance measurement module 106, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 106, at any given time.

Processor 80 receives signals indicative of impedance of a lead and signals indicative of motion of the lead. Based upon the signals, e.g., data derived from the signals, processor 80 can monitor a parameter indicative of impedance of the lead and a parameter indicative of motion of the lead in order to determine whether there is a correlation between the parameter indicative of impedance of the lead and the parameter indicative of motion of the lead. If processor 80 identifies a correlation between the parameter indicative of impedance of the lead and the parameter indicative of motion of the lead, processor 80 may determine that a lead related condition, such as a fractured conductor, exists. In some examples, electrical sensing module 86 and/or sensor 87 may generate the signals indicative of impedance and motion of the lead, and processor 80 may receive the signals from electrical sensing module 86 and/or sensor 87.

A signal indicative of impedance of a lead can be a signal that directly or indirectly represents the impedance of one or more conductors within the lead. That is, in some examples, the signal indicative of impedance of the lead comprises measured values of impedance of one or more conductors within the lead and, in other examples, the signal indicative of impedance of the lead is a signal that is primarily indicative of a physiological parameter and used for another purpose, e.g., to monitor physiological activity of patient 14. In some examples, electrical sensing module 86 provides signals that directly represent the impedance of one or more conductors within the lead, e.g., signals provided to processor 80 by impedance measurement module 106. In other examples, electrical sensing module 86 provides signals that indirectly represent the impedance of one or more conductors within the lead. For example, electrical sensing module 86 may provide processor 80 one or more signals indicative of electrical activity of heart 12, e.g., EGMs, from which processor 80 can derive information about the impedance of one or more conductors within the lead.

In examples in which electrical sensing module 86 provides signals that directly represent the impedance of one or more conductors within the lead, sensing module 86 and/or processor 80 are capable of collecting, measuring, and/or calculating impedance data for any of a variety of electrical paths that include two or more of electrodes 40, 42, 44, 46, 48, 50, 58, 62, 64 and 66. In such examples, impedance measurement module 106 may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 106. In particular, ADC 108 may digitize parameter values measured by impedance measurement module 106, and processor 80 may determine impedance values based on the digitized parameter values. In some examples, processor 80 stores the impedance values in memory 82A or 82B.

In some examples, processor 80 may perform an impedance measurement by controlling delivery, from signal generator 84, of a voltage pulse between first and second electrodes. Impedance measurement module 106 may measure a resulting current, and processor 80 may calculate a resistance based upon the voltage amplitude of the pulse and the measured amplitude of the resulting current as digitized by ADC 108. In other examples, processor 80 may perform an impedance measurement by controlling delivery, from signal generator 84, of a current pulse between first and second electrodes. Impedance measurement module 106 may measure a resulting voltage, and processor 80 may calculate a resistance based upon the current amplitude of the pulse and the measured amplitude of the resulting voltage as digitized by ADC 108. Impedance measurement module 106 may include circuitry for measuring amplitudes of resulting currents or voltages, such as sample and hold circuitry.

In these examples of performing impedance measurements, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

Signal generator 84 may deliver signals and measure impedance at a frequency equal to or greater than an expected frequency of lead motion, such that changes in impedance due to lead motion can be detected. That is, as discussed in further detail above, lead motion can affect lead impedance in some examples. Consequently, in order to detect changes in lead impedance due to lead motion, the frequency of delivery of sub-threshold pulses for measurement of impedance can be greater than the frequency of expected lead motion.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

Additionally or alternatively, electrical sensing module 86 may provide signals indicative of electrical activity of heart 12 from which processor 80 can also derive information about the impedance of one or more conductors within the lead. For example, fluctuations in such signals indicative of electrical activity of heart 12 may correspond to fluctuations in the impedance of one or more conductors within the lead. In some examples, narrow band channels 102 and/or wide band channel 104 of electrical sensing module 86 facilitate generation of signals indicative of electrical activity of heart 12, which signals may also fluctuate as a function of changing impedance of one or more conductors within one or more leads.

Each of narrow band channels 102 may comprise a narrow band filtered sense-amplifier that compares the signal sensed by a pair of electrodes to a threshold. If the filtered and amplified signal is greater than the threshold, the narrow band channel indicates that a certain electrical heart event has occurred. Processor 80 can use that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing electrode configuration of electrodes 40 and 42, which are used for sensing and/or pacing in right ventricle 28 of heart 12. Another narrow band channel 102 may include another R-wave amplifier that receives signals from the sensing electrode configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Wide band channel 104 may comprise an amplifier with a relatively wider pass band than the R-wave or P-wave amplifiers. Signals from the sensing electrode configuration that is selected for coupling to this wide-band amplifier may be converted to multi-bit digital signals by ADC 108. In some examples, processor 80 may store the digitized versions of signals from wide band channel 104 in memory 82B as EGMs.

The amplifiers of channels 102 and 104 may be differential amplifiers configured to detect relatively low energy signals, e.g., the electrical activity of the heart. To facilitate sensing via a differential amplifier, there may be a typical load, e.g., about 500 ohms, between the two inputs to the differential amplifier, which may be coupled by respective conductors to a pair of electrodes 40, 42, 44, 46, 48, 50, 58, 62, 64 and 66. If the impedance of conductors associated with either electrode changes, the output of the differential amplifier will respond with a signal variation, the amplitude of which may be proportional to the magnitude of the change in the impedance. In situations in which the impedance change corresponds to motion of one or more leads, as described herein, the signal variation due to the impedance changes may be a parameter indicative of impedance or be analyzed to identify one or more parameters indicative of impedance. A threshold, e.g., amplitude, may be used to distinguish between normal EGM variation and signal variation due to impedance changes, e.g., impedance changes correlated to or caused by lead motion.

Processor 80 may receive a version of the signal provided by one of channels 102 and 104 that has been digitized by ADC 108, which signal indicates the impedance of one or more conductors of one or more leads, and analyze the signal to identify a parameter indicative of the impedance. In the illustrated example, processor 80 receives a digitized version of the signal provided by wide band channel 104. The channel may be selectively coupled to any combination, e.g., pair, of electrodes 40, 42, 44, 46, 48, 50, 58, 62, 64 and 66, by switching module 100, which may be controlled by processor 80, in order to analyze a variety of signals to identify parameters indicative of impedance for various conductors coupled to various ones of the electrodes.

Processor 80 also receives signals and/or data indicative of motion of the lead. In some examples, electrical sensing module 86, sensor 87, or another component of system 10 generates an electrical signal that is indicative of motion of the lead and transmits the signal to processor 80.

In examples in which the lead is implanted proximate to or within heart 12 of patient 14, motion of the lead may directly correspond to mechanical activity of heart 12. As discussed previously, sensor 87 generates a signal indicative of mechanical activity of heart 12. Consequently, in some examples, in order to monitor the motion of the lead, processor 80 receives a signal generated by sensor 87.

As another example, the signal indicative of motion of the lead may be a signal that is indicative of electrical activity of heart 12, because mechanical activity of heart 12 may directly correspond to, e.g., may result from, electrical activity of heart 12. For example, electrical sensing module 86 can generate a signal that represents atrial and ventricular electrical activity of heart 12, e.g., an EGM, sensed via one or more of electrodes 40, 42, 44, 46, 48, 50, 58, 62, 64, or 66. Processor 80 can extract information related to the mechanical activity of heart 12 from the signal, such as information related to the cycle of contractions that are initiated by the electrical activity of heart 12, e.g., the frequency of contractions. In some examples, processor may receive indications of P- or R-waves from one of narrow band channels 102, and estimate or determine the occurrence or frequency of mechanical contractions, and thus motion of the lead, based on the indications. In some examples, processor 80 additionally or alternatively estimates or determines the occurrence or frequency of mechanical contractions of heart 12 based on the delivery of pacing pulses to heart 12 by signal generator 84.

Additionally or alternatively, the signal indicative of motion of the lead is representative of motion that is unrelated to the mechanical activity of heart 12. For example, motion of another portion of the body of patient 14, e.g., motion of a torso or limb of patient 12, can, in some examples, affect, e.g., cause, motion of the lead. Thus, processor 80 may receive a signal from one or more implantable or external activity sensors 103 that generate an electrical signal indicative of patient motion that is unrelated to mechanical activity of heart 12. For example, the activity sensors 103 may generate a signal related to the change in acceleration of patient 14 in multiple directions, e.g., in an x-axis direction, a y-axis direction, and a z-axis direction.

In some examples, the activity sensors 103 are implanted within a region of patient 14 that is substantially near the portion of the body of patient 14 within which the lead is implanted and, consequently, the activity sensors 103 generate a signal representative of motion of the portion of the body within which the lead is implanted. As an example, if the lead is implanted proximate to or within heart 12, one or more activity sensors 103 can be implanted within the torso of patient 14 and may generate a signal indicative of motion of the torso of patient 14. The signal generated by the one or more activity sensors 103 implanted within the torso of patient 14 may be representative of motion of the lead because the lead is implanted within the torso of patient 14.

In other examples, the activity sensors 103 are placed externally on the body of patient 14, e.g., are not implanted within patient 14. In these examples, the activity sensors 103 generate electrical signals indicative of motion of the particular portion of the body on which the activity sensors 103 are placed. For example, an activity sensor 103 may be positioned on a portion of the body of patient 14 which exhibits motion that corresponds to motion of the lead, e.g., on the waist of patient 14, and may consequently generate a signal indicative of motion of the lead. The signals provided by sensors 87 and 103 may be digital signals, or may be provided to ADC 108 for conversion to digital signals prior to analysis by processor 80.

Processor 80 can identify a lead related condition based on a correlation between impedance and motion of the lead. In order to identify a correlation between impedance and motion of the lead, processor 80 monitors one or more parameters indicative of impedance of the lead and one or more parameters indicative of motion of the lead. In some examples, a parameter indicative of impedance may be an aspect or a component of a signal that indicates the impedance of the lead. For example, in some examples, a parameter indicative of impedance is a characteristic of a signal indicative of impedance, e.g., a frequency, phase, or amplitude that defines a signal indicative of impedance. Similarly, a parameter indicative of motion may be an aspect or a component of a signal indicative of motion of the lead. In some examples, the parameter indicative of motion is a characteristic of a signal indicative of motion, e.g., a frequency, phase, or amplitude that defines a signal indicative of motion of the lead. By monitoring parameters representative of impedance and motion of the lead, processor 80 can determine whether there is a correlation between one or more parameters indicative of impedance of the lead and one or more parameters indicative of motion of the lead. For purposes of description only, processor 80 is described herein as identifying a correlation between the frequency and the phase of a signal indicative of impedance of a lead and the frequency and phase of a signal indicative of motion of the lead. However, in other examples, the parameters indicative of impedance and motion can be parameters other than frequency and phase that are representative of impedance and motion, respectively, of the lead.

As discussed previously, in some examples, the signal indicative of impedance of the lead can be a signal that is directly representative of the impedance of one or more conductors of the lead while, in other examples, the signal indicative of impedance of the lead can be derived from a signal that is not necessarily directly representative of the impedance of one or more conductors of the lead, such as an EGM. In examples in which the signal indicative of impedance of the lead is directly representative of the impedance of one or more conductors of the lead, processor 80 monitors the frequency and phase of the signal indicative of impedance. Alternatively, in some examples in which the signal is indirectly representative of impedance of the lead, processor 80 may monitor the frequency and phase of fluctuations in the signal. For example, in examples in which processor 80 monitors the EGM signal in order to monitor the impedance of the lead, processor 80 may monitor the frequency and phase of fluctuations in the EGM signal that result from changes in impedance of the lead caused by the motion of the lead. In addition, processor 80 also monitors the frequency and phase of the signal indicative of motion of the lead.

In some examples, processor 80 continuously receives and analyzes the signal indicative of impedance, e.g., from electrical sensing module 86, and continuously determines the frequency and phase of the signal indicative of impedance in order to monitor the frequency and phase. Processor 80 may also continuously receive and analyze a signal indicative of motion of the lead, e.g., from electrical sensing module 86, sensor 87, or activity sensor 103, and continuously determine the frequency and phase of the signal.

In some examples, instead of or in addition to monitoring signal data continuously, processor 80 can analyze signal data that has previously been stored in memory 82A or 82B. That is, processor 80 can, in some examples, access signal data stored in memory 82A or 82B and analyze the signal data at a point in time after the signal data has been collected in order to determine whether there is a correlation between frequency and phase of a signal indicative of impedance of a lead and a signal indicative of motion of the lead. For example, processor 80 may access and analyze signal data stored as impedance parameter data 94 and motion parameter data 96 of memory 82A (FIG. 4A) or EGM data 100 and cardiac mechanical activity data 102 of memory 82B (FIG. 4B).

In order to identify a correlation between the frequency and phase of a signal indicative of impedance of a lead and a signal indicative of motion of the lead, processor 80 analyzes a segment of the signal indicative of impedance of the lead and a segment of the signal indicative of motion of the lead that were sensed during substantially the same time period. For example, processor 80 can determine the frequency of the segment of the signal indicative of impedance of the lead and the frequency of the segment of the signal indicative of motion of the lead. Processor 80 can also determine whether the segments of signal data are in phase, e.g., whether the segments of signal data illustrate a similar pattern of amplitude change over several cycles of oscillations. Processor 80 may determine that the frequencies of the segments of signal data are the same and that the segments of signal data illustrate signals that are in phase. Based on the analysis, processor 80 may determine that there is a correlation between the frequency and phase of the signal indicative of impedance of the lead and the frequency and phase of the signal indicative of motion of the lead. As discussed previously, in some examples, a correlation between a parameter indicative of impedance of the lead and a parameter indicative of motion of the lead can indicate that a lead related condition, such as a fractured conductor, exists.

In some examples, subsequent to determining that a lead related condition exists, processor 80 may control IMD 16 to modify sensing or therapy parameters. Additionally or alternatively, processor 80 may send an alert to programmer 24 in order to notify a user, e.g., a clinician, that a lead related condition may exist.

Figure 6:
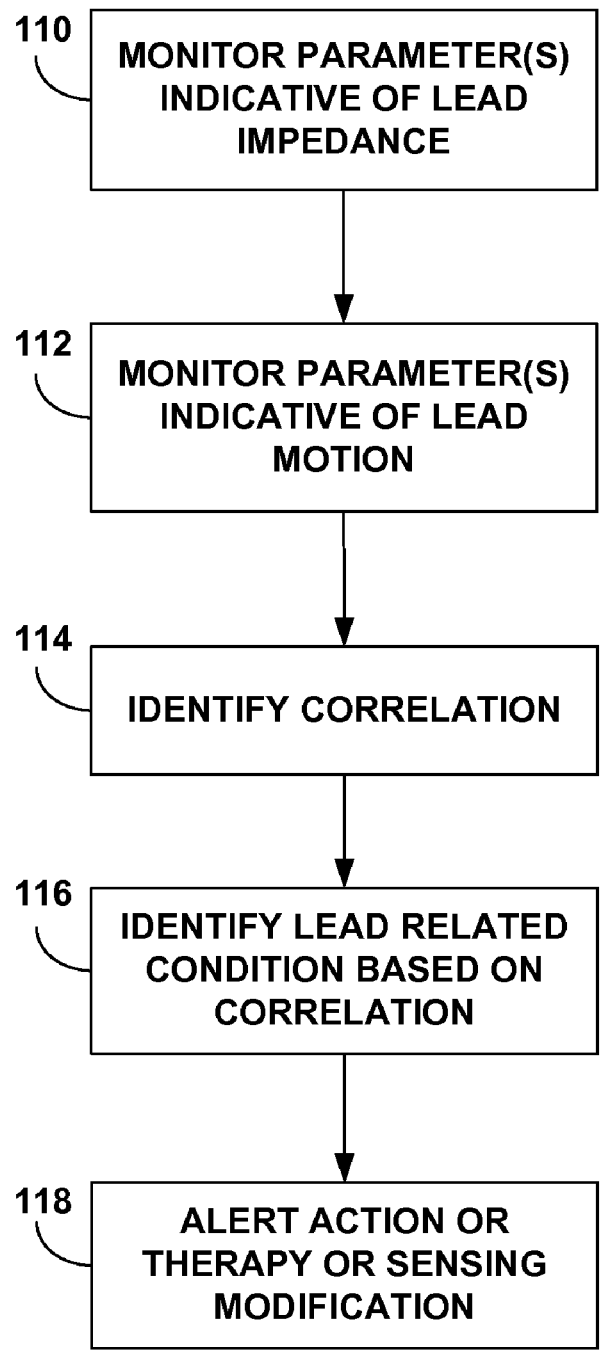
FIG. 6 is a flow diagram illustrating an example technique for identifying a lead related condition based on a correlation between a parameter indicative of lead impedance and a parameter indicative of lead motion.

FIG. 6 is a flow diagram illustrating an example technique for identifying a lead related condition based on a correlation between a parameter indicative of impedance of a lead and a parameter indicative of motion of the lead. While FIG. 6 is described as being performed by processor 80 of IMD 16, in other examples, a processor of another device described herein, e.g., programmer 24, can automatically perform any part of the technique shown in FIG. 6 alone or with the aid of a user.

In the example technique illustrated in FIG. 6, processor 80 monitors one or more parameters indicative of impedance of the lead (110). In some examples, processor 80 receives a signal that is indicative of impedance of a lead of system 10 from another component of system 10 that sensed the signal, e.g., electrical sensing module 86. As discussed previously with respect to FIG. 5, the signal may directly or indirectly represent the impedance of one or more conductors of the lead. In some examples, processor 80 monitors one or more defining characteristics of the signal indicative of impedance of the lead, such as the frequency and the phase of the signal indicative of impedance of the lead. Processor 80 can continuously analyze the signal to quantify various characteristics of the signal. In some examples, processor 80 accesses signal data stored in memory 82A or 82B in order to monitor the parameter indicative of impedance.

Processor 80 also monitors a parameter indicative of motion of the lead (112). In some examples, processor 80 receives a signal indicative of motion of the lead from another component of system 10, e.g., electrical sensing module 86, sensor 87, or activity sensor 103. In some examples, processor 80 monitors one or more defining characteristics of the signal indicative of motion of the lead, such as the frequency and the phase of the signal. Processor 80 can continuously analyze the signal and, in some examples, processor 80 accesses signal data stored in memory 82A or 82B in order to monitor the parameter indicative of motion of the lead.

In the example illustrated in FIG. 6, processor 80 identifies a correlation between the parameter indicative of impedance of the lead and the parameter indicative of motion of the lead (114). For example, in some examples, processor 80 determines that a segment of the signal indicative of motion of the lead and a segment of the signal indicative of impedance of the lead that were sensed at substantially the same time illustrate common defining characteristics, e.g., the signals are defined by the same frequency and are in phase. In some examples, processor 80 may determine that a characteristic of the signal indicative of impedance of the lead and a characteristic of the signal indicative of motion of the lead have substantially the same value, e.g., processor 80 can measure a value of the characteristic and determine that the values of the characteristic are the same for both signals.

If processor 80 identifies a correlation between the parameter indicative of impedance of the lead and the parameter indicative of motion of the lead, processor 80 may determine that a lead related condition exists (116). For example, if processor 80 identifies a correlation between a characteristic of the signal indicative of impedance of the lead and a characteristic of the signal indicative of motion of the lead generated during the same period of time, processor 80 may determine that a condition has occurred that affected the impedance of one or more conductors of the lead, e.g., a conductor fracture.

Upon determining that a lead related condition exists, processor 80 may initiate therapy or sensing modifications based on the existence of the lead related condition. For example, processor 80 may instruct signal generator 84 to stop delivering stimulation through a fractured conductor. Processor 80 may also instruct sensing module 86 and/or sensor 87 to discontinue sensing through a fractured conductor. Alternatively or additionally, processor 80 sends an alert to programmer 24 (FIG. 1) or to another external device to notify a user that a lead related condition has been detected (118).

Figure 7:
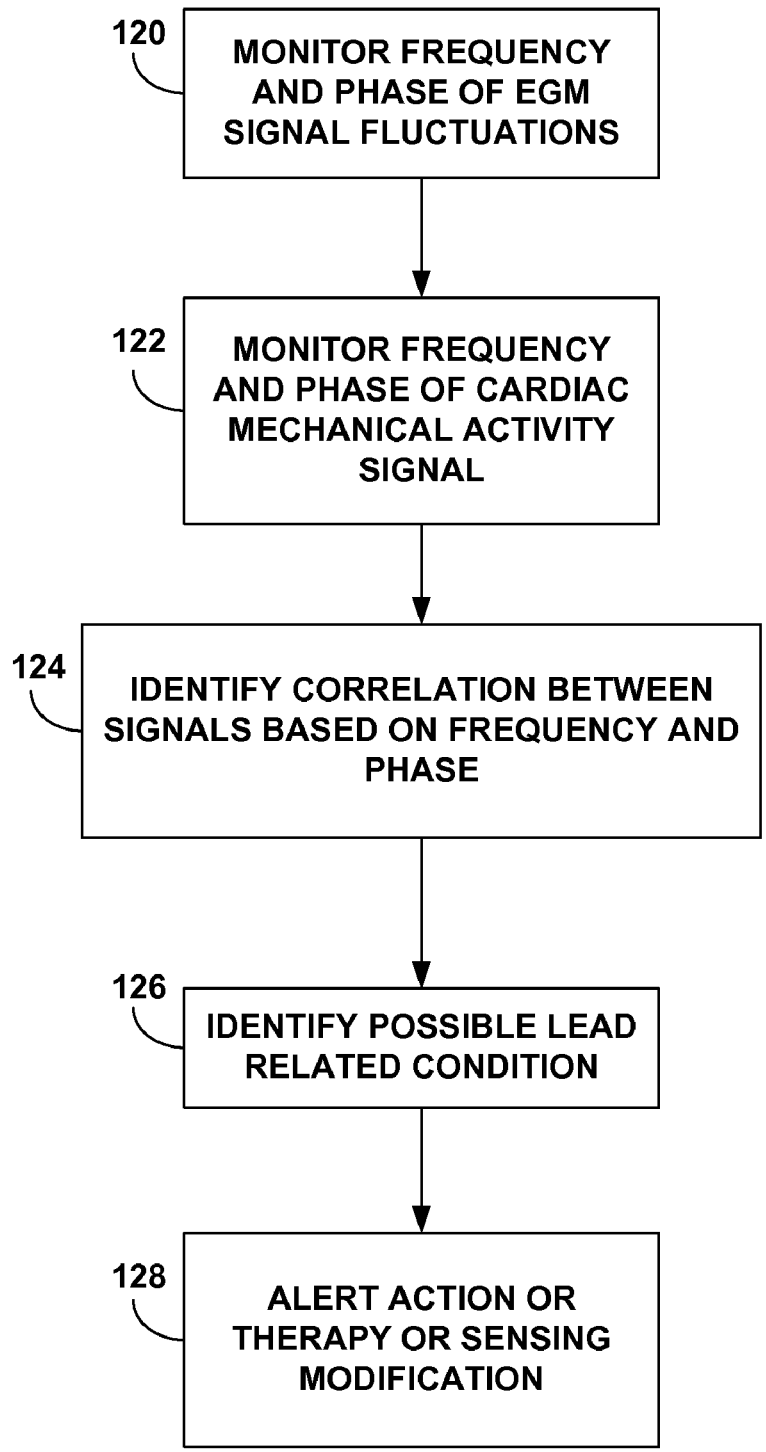
FIG. 7 is a flow diagram illustrating an example technique for identifying a lead related condition based on a correlation of frequency and phase between particular electrical signals.

FIG. 7 is a flow diagram illustrating another example technique for identifying a lead related condition of the lead based on a correlation between frequency and phase of signal indicative of impedance of a lead and frequency and phase of a signal indicative of motion of the lead. While FIG. 7 is described as being performed by processor 80 of IMD 16, in other examples, a processor of another device, e.g., programmer 24, can automatically perform any part of the technique shown in FIG. 7 alone or with the aid of a user.

In the example illustrated in FIG. 7, processor 80 monitors the frequency and phase of fluctuations in an EGM signal (120), which is indicative of atrial and ventricular electrical activity of heart 12. As discussed previously, the fluctuations in the EGM signal may correspond to changes in the impedance of the lead that senses the EGM signal. In addition to monitoring the EGM signal, processor 80 monitors the frequency and phase of a signal indicative of mechanical activity of heart 12 (122). The signal indicative of mechanical activity of heart 12 may, for example, be a signal sensed by sensor 87, which may be any sensor that generates a signal that represents the mechanical activity of heart 12. The mechanical activity of heart 12 may be representative of the motion of the lead in examples in which the lead is implanted within or proximate to heart 12. Consequently, the signal indicative of mechanical activity of heart 12 can be a signal indicative of motion of the lead.

Processor 80 may identify a correlation between the frequency and phase of the EGM signal and the frequency and phase of the signal indicative of mechanical activity of heart 12 (124). For example, processor 80 may determine that the signals have the same frequency and are in phase. Similar frequency and phase characteristics of the two signals may indicate that the impedance changes of the conductors within the lead and the motion of the lead are in phase.

Upon identifying a correlation between the frequency and phase of the EGM signal fluctuations and the cardiac mechanical activity signal, processor 80 determines that a lead related condition exists (126). As with the example technique illustrated in FIG. 6, processor 80 may send instructions to signal generator 84, sensing module 86, or sensor 87 to initiate therapy or sensing modifications based on the existence of the lead related condition. Alternatively or additionally, processor 80 can send an alert to programmer 24 (FIG. 1) or to another external device to notify a user that a lead related condition has been detected (128).

Figure 8:
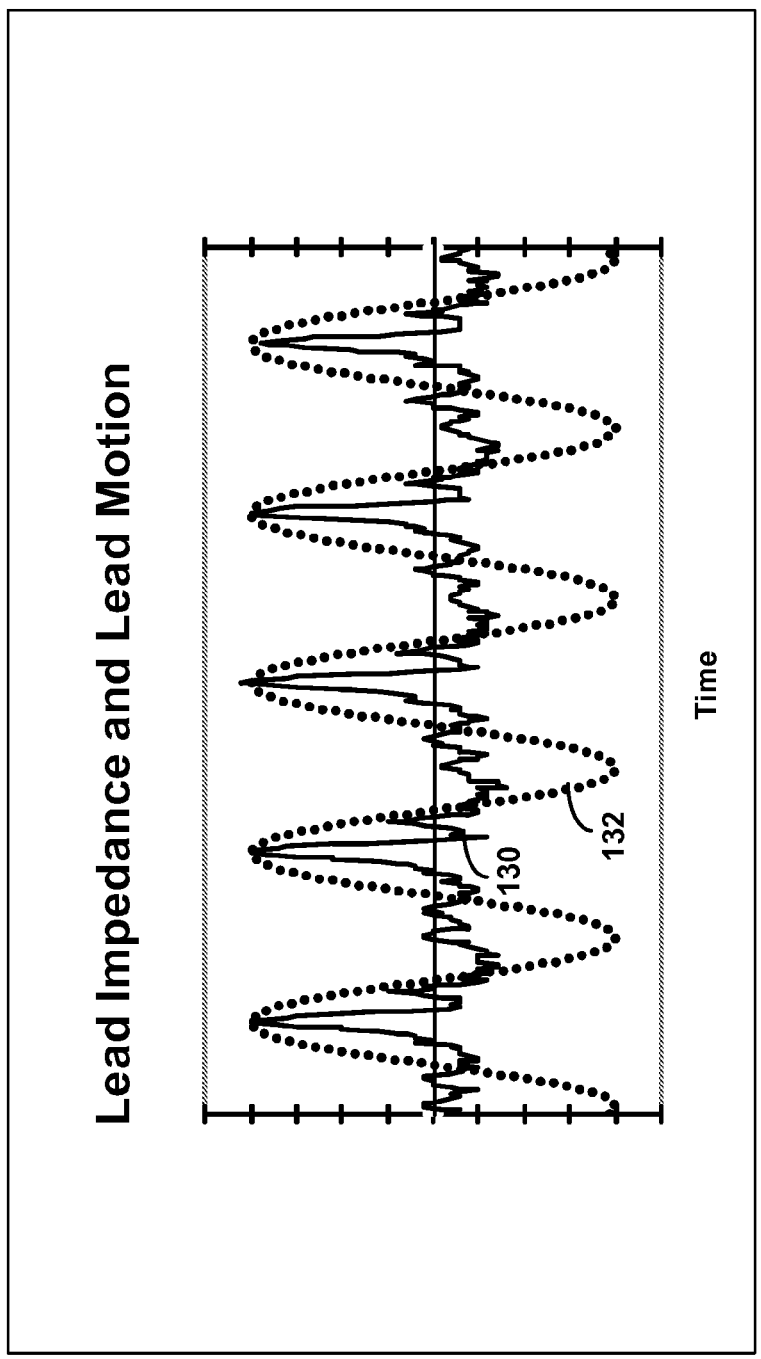
FIG. 8 is a graph illustrating a correlation of parameters indicative of impedance of a lead and parameters indicative of motion of the lead.

FIG. 8 is a graph illustrating a correlation between characteristics of a signal indicative of impedance of a lead and characteristics of a signal indicative of motion of the lead. In the example illustrated in FIG. 8, signal 130 is indicative of impedance of the lead and the signal 132 is indicative of motion of the lead. For example, signal 130 may be a signal that directly or indirectly represents the impedance of one or more conductors, e.g., a signal representative of fluctuations within an EGM signal, within the lead and signal 132 may be a signal that corresponds to mechanical activity of heart 12 that can be representative of motion of the lead.

A processor, e.g., processor 80 of IMD 16, may analyze signals 130 and 132 and determine that a frequency of signal 130 and a frequency of signal 132 are the same. In addition, the processor may determine that signal 130 and signal 132 are in phase, e.g., there is no offset between the beginning of a cycle of signal 130 and the beginning of cycle of signal 132. As used herein, the frequency of a signal can be characterized as the number of cycles per unit time. Two signals can be described as being in phase if similar points in the cycles of the signals occur at substantially the same point in time. Based on the correlation between the frequency and phase of signal 130 and signal 132, a processor may determine that a lead related condition exists within the lead.

Figure 9:
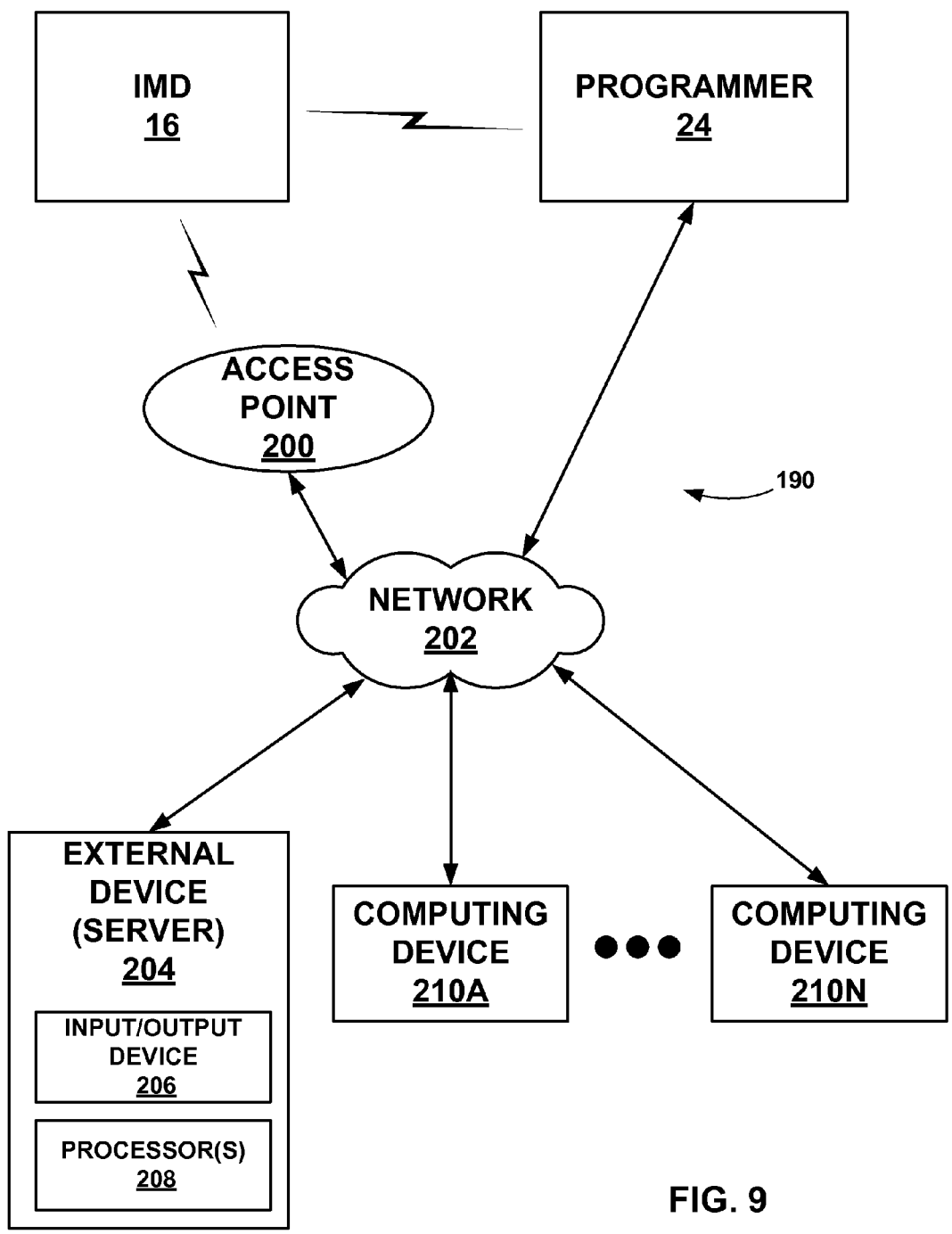
FIG. 9 is a block diagram illustrating an example system that includes an external device, such as a server, and one or more computing devices that are coupled to the IMD and programmer shown in FIG. 1 via a network.

FIG. 9 is a block diagram illustrating an example system 190 that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 9, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 9, server 204 may comprise one or more processors 208 and an input/output device 206, which need not be co-located.

Server 204 may, for example, practice the methods described herein for determining whether a lead related condition exists. Server 204 may acquire data related to the impedance of the lead and data related to the motion of the lead, determine whether a correlation exists between a parameter indicative of impedance of the lead and a parameter indicative of motion of the lead, and identify a lead related condition based on the correlation. Server 204 may implement any or all of the modules illustrated in FIGS. 4A and 4B. Furthermore, in some examples in which IMD 16 determines whether a lead related condition exists as described above, server 204 may provide a database for storing data related to signals indicative of impedance of the lead and signals indicative of motion of the lead within an external storage unit or memory, which may be provided by server 204 as one example, or by programmer 24 as another.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or one or more of the computing devices 210A-210N may perform any of the various functions or operations described herein.

Network 202 may comprise a local area network, wide area network, or global network, such as the Internet. In some cases, programmer 24 or server 204 may assemble data related to impedance of the lead and data related to motion of the lead, e.g., data collected during particular periods of time, in web pages or other documents for viewing by patients and/or trained professionals, such as clinicians, via viewing terminals associated with computing devices 210A-210N. System 190 may be implemented, in some aspects, with general network technology and functionality similar to that provided by the Medtronic CareLink® Network developed by Medtronic, Inc., of Minneapolis, Minn.

Although the disclosure is described with respect to cardiac stimulation therapy, such techniques may be applicable to other therapies in which lead integrity is important, such as, e.g., spinal cord stimulation, deep brain stimulation, pelvic floor stimulation, gastric stimulation, occipital stimulation, functional electrical stimulation, and the like. In such therapies, the techniques described in this disclosure may be applied to detect possible lead-related conditions.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
monitoring a parameter indicative of impedance of a lead, wherein monitoring the parameter indicative of impedance of the lead comprises monitoring at least one of a frequency or a phase of a signal indicative of impedance of the lead;
monitoring a parameter indicative of motion of the lead, wherein monitoring the parameter indicative of motion of the lead comprises monitoring at least one of a frequency or a phase of a signal indicative of motion of the lead;
identifying a correlation between the parameter indicative of impedance of a lead and the parameter indicative of motion of the lead by at least one of:
 determining that the frequency of the signal indicative of impedance of the lead and the frequency of the signal indicative of motion of the lead are substantially the same, or
 determining that the signal indicative of impedance of the lead and the signal indicative of motion of the lead are in phase; and
identifying a lead related condition based on the correlation.

2. The method of claim 1, wherein the signal indicative of impedance of a lead comprises a signal indicative of electrical activity of a heart sensed via the lead.

3. The method of claim 1, wherein the signal indicative of motion of the lead comprises a signal indicative of mechanical activity of a heart of a patient.

4. The method of claim 1, wherein the signal indicative of motion of the lead comprises a signal indicative of motion of the patient.

5. The method of claim 1, wherein monitoring the parameter indicative of motion of the lead comprises monitoring delivery of pacing pulses to a heart.

6. The method of claim 1, wherein identifying a correlation between the parameter indicative of impedance of a lead and the parameter indicative of motion of the lead comprises determining that a value of the parameter indicative of impedance of a lead and a value of the parameter indicative of motion of the lead are correlated during a particular period of time.

7. The method of claim 1, further comprising providing an alert in response to identifying the lead related condition.

8. The method of claim 1, further comprising modifying a therapy in response to identifying the lead related condition.

9. The method of claim 1, further comprising modifying at least one parameter associated with detection of the cardiac events based on detecting the lead related condition.

10. A system comprising:
a module that provides a signal indicative of impedance of a lead; and
a processor that:
 receives the signal,
 monitors a parameter indicative of impedance of a lead based on the signal, wherein the parameter indicative of impedance of a lead comprises at least one of a frequency or a phase of the signal indicative of impedance of the lead,
 monitors a parameter indicative of motion of the lead, wherein the parameter indicative of motion of the lead comprises at least one of a frequency or a phase of a signal indicative of motion of the lead,
 identifies a correlation between the parameter indicative of impedance of the lead and the parameter indicative of motion of the lead by at least determining that the frequency of the signal indicative of impedance of the lead and the frequency of the signal indicative of motion of the lead are substantially the same, or determining that the signal indicative of impedance of the lead and the signal indicative of motion of the lead are in phase, and
 identifies a lead related condition based on the correlation.

11. The system of claim 10, wherein the module comprises an impedance measurement module that measures the impedance of the lead and provides the signal indicative of impedance of the lead based on the measurement.

12. The system of claim 10, wherein the signal indicative of impedance of the lead comprises a signal indicative of electrical activity of a heart.

13. The system of claim 10, further comprising a sensor that generates the signal indicative of motion of the lead.

14. The system of claim 10, wherein the signal indicative of motion of the lead comprises a signal indicative of motion of the heart.

15. A system comprising:
means for monitoring a parameter indicative of impedance of a lead, wherein the means for monitoring a parameter indicative of impedance of a lead monitors at least one of a frequency or a phase of a signal indicative of impedance of the lead;
means for monitoring a parameter indicative of motion of the lead, wherein the means for monitoring a parameter indicative of motion of the lead monitors at least one of a frequency or a phase of a signal indicative of motion of the lead;
means for identifying a correlation between the parameter indicative of impedance of a lead and the parameter indicative of motion of the lead, wherein the means for identifying the correlation comprises at least one of:

means for determining that the frequency of the signal indicative of impedance of the lead and the frequency of the signal indicative of motion of the lead are substantially the same, or means for determining that the signal indicative of impedance of the lead and the signal indicative of motion of the lead are in phase; and means for identifying a lead related condition based on the correlation.

16. The system of claim 15, wherein the means for identifying a correlation identifies a correlation between the parameter indicative of impedance of a lead and the parameter indicative of motion of the lead by determining that a value of the parameter indicative of impedance of a lead and a value of the parameter indicative of motion of the lead are correlated during a particular period of time.

17. A computer-readable storage medium comprising instructions that cause a processor to:

monitor a parameter indicative of impedance of a lead, wherein the parameter indicative of impedance of a lead comprises at least one of a frequency or a phase of a signal indicative of impedance of the lead;

monitor a parameter indicative of motion of the lead, wherein the parameter indicative of motion of the lead comprises at least one of a frequency or a phase of a signal indicative of motion of the lead;

identify a correlation between the parameter indicative of impedance of a lead and the parameter indicative of motion of the lead by at least determining that the frequency of the signal indicative of impedance of the lead and the signal indicative of motion of the lead are substantially the same, or determining that the signal indicative of impedance of the lead and the signal indicative of motion of the lead are in phase; and identify a lead related condition based on the correlation.

* * * * *